United States Patent [19]

Okada

[11] Patent Number: 4,961,208

[45] Date of Patent: Oct. 2, 1990

[54] COMPUTED TOMOGRAPHY APPARATUS

[75] Inventor: Hiroyuki Okada, Sizuoka, Japan

[73] Assignee: Hamamatsu Photonics K. K., Shizuoka, Japan

[21] Appl. No.: 475,878

[22] Filed: Feb. 6, 1990

[30] Foreign Application Priority Data

Feb. 7, 1989 [JP] Japan .................................... 1-28231

[51] Int. Cl.⁵ ............................................ G01N 23/00
[52] U.S. Cl. ...................................... 378/17; 378/20; 250/363.04
[58] Field of Search ................ 370/17, 20; 250/363.04

[56] References Cited

U.S. PATENT DOCUMENTS 4,316,091 2/1982 Bernardi ................................ 378/17

Primary Examiner—Craig E. Church
Attorney, Agent, or Firm—Finnegan, Henderson, Farabow, Garrett, and Dunner

[57] ABSTRACT

A gantry and a subject holder on which a subject can be fixed in his sitting position are supported on a main frame. A gantry drive unit moves the gantry to a position of examination and also drives it until an inclination angle for examination is reached. A computing unit performs mathematical operations based on the data representing the inclination angle of the gantry and produces a control signal for controlling a holder moving direction which is determined in accordance with the inclination angle. A moving unit moves the holder and a subject fixed thereon in the holder moving direction in response to the control signal.

7 Claims, 3 Drawing Sheets

COMPUTED TOMOGRAPHY APPARATUS

BACKGROUND OF THE INVENTION

The present invention relates to an X-ray or positron computed tomography (CT) apparatus which is so designed that a subject to be examined can be slid into a tunnel in a gantry while he is in a sitting position.

FIGS. 6 and 7 show a recently proposed positron CT apparatus capable of high resolution. As shown, it consists generally of a gantry 1 in an annular form and a holder 3 such as a bed for fixing a subject 2. The gantry 1 consists of an annular array of sectorial radiation detecting cassettes 4a for detecting gamma-rays. Every cassette contains four units of radiation detector 4 each consisting of a scintillator 5 and a photomultiplier tube 6. These cassettes are superposed in five stacks. The radiation detectors 4 are provided with shield collimators 7 and 8. As shown specifically in FIG. 7, the shield collimator 7 is provided on the inner side of the gantry and the shield collimator 8 on its outer side so as to reduce the entry of background noise (i.e., scattered rays or a single gamma-ray) coming from areas other than the site to be examined. The radiation detectors 4 are also provided with a slice collimator 9 for each scintillator 5.

The conventional CT apparatus are intended to perform diagnosis with the subject being fixed in a supine position on a holder which is shaped like a sleeping bed. With such apparatus, it has been easy to cause the subject to slide into a tunnel in a gantry. However, as the use of high-resolution positron CT apparatus has increased these days in order to examine the head of a subject, there has arisen a growing need for examination with the subject being in a sitting position. In the conventional CT apparatus, adjustments for the straight movement and rotation of the gantry are performed independently of adjustments for the horizontal and vertical movements of the holder, and if the apparatus uses a small-diameter tunnel as in a CT apparatus designed to examine the head, it has been quite tedious and has required considerable skill to insure that the head of the subject who is in a sitting position is slid into the tunnel without bumping against its inner surface. Further, a projector for correct positioning of the head cannot be installed within the tunnel because of its small diameter.

SUMMARY OF THE INVENTION

An object, therefore, of the present invention is to provide an apparatus that enables a subject to be slid easily into the tunnel of a gantry and correctly positioned for diagnosis irrespective of whether he is in a supine or sitting position.

The above-stated object of the present invention can generally be attained by a CT apparatus in which a gantry having a tunnel for examining a subject and a subject holder are supported on a main frame. This apparatus further includes a gantry drive unit which not only moves said gantry to a position of examination but also drives it until an angle of inclination for examination is reached, a computing unit which performs mathematical operations based on the data representing the angle of inclination of the gantry set by said gantry drive unit and which produces an output signal for controlling the direction in which said holder is to be moved, and a moving unit for moving said holder at a predetermined angle in response to the output signal from said computing unit.

When a subject is to be examined while he is in a sitting position, he is first seated on a holder such as a chair, and after having his body and head fixed, the head is brought close to the gantry. Using respective cross patterns of light from three projectors incorporated at the entrance of the gantry to perform positioning of the head, the axis of the subject is made coincident with the axis of the tunnel.

These procedures set the angle of inclination of the gantry. The computing unit performs mathematical operations based on the data representing this angle and sends an output signal to the unit for moving the holder. In response to the output signal, the unit moves the holder in a desired direction. As a result, the subject can be slid into the tunnel in alignment with the axis of the tunnel.

DETAILED DESCRIPTION OF THE PREFERRED EMBODIMENTS

Two preferred embodiments of the present invention are described below with reference to the accompanying drawings.

Figure 1:
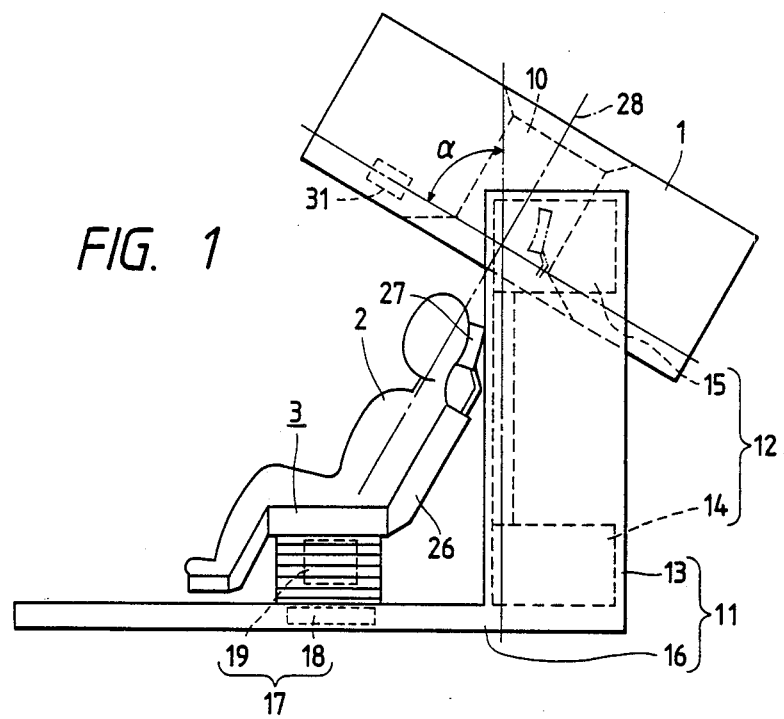
FIG. 1 is a front view of a CT apparatus according to a first embodiment of the present invention.
Figure 6:
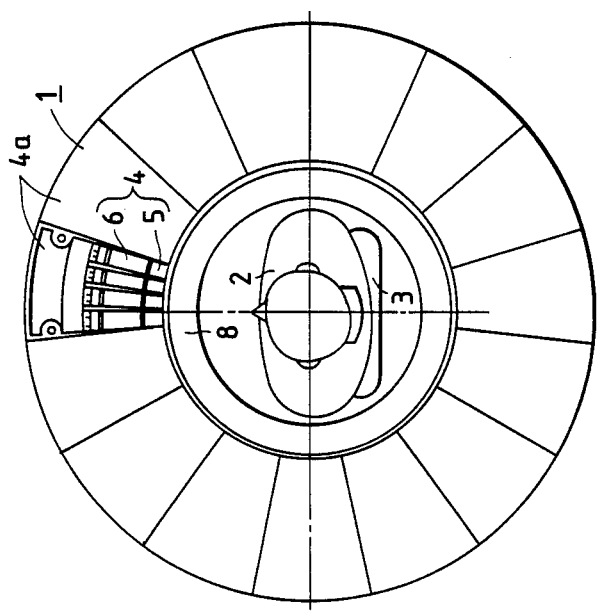
FIG. 6 is a side view of a gantry of a recently proposed CT apparatus.

Shown by 1 in FIG. 1 is a gantry which is assumed here to be identical in construction to that shown in FIG. 6. Gantry 1 is installed on a main frame 11 in such a way that it is vertically movable and rotatable by means of a drive unit 12. The main frame 11 has erect support legs 13 in which is provided the drive unit 12 consisting of a sub-unit 14 for driving the gantry 1 in a vertical direction and a sub-unit 15 for driving it to rotate. The main frame 11 also has rails 16 on which is provided a unit 17 for moving the subject holder 3 which can serve both as a chair and as a bed. The moving unit 17 consists of a horizontal moving sub-unit 18 which moves horizontally along the rails 16 and a vertical moving sub-unit 19 which is capable of extending or retracting in a vertical direction.

Figure 2:
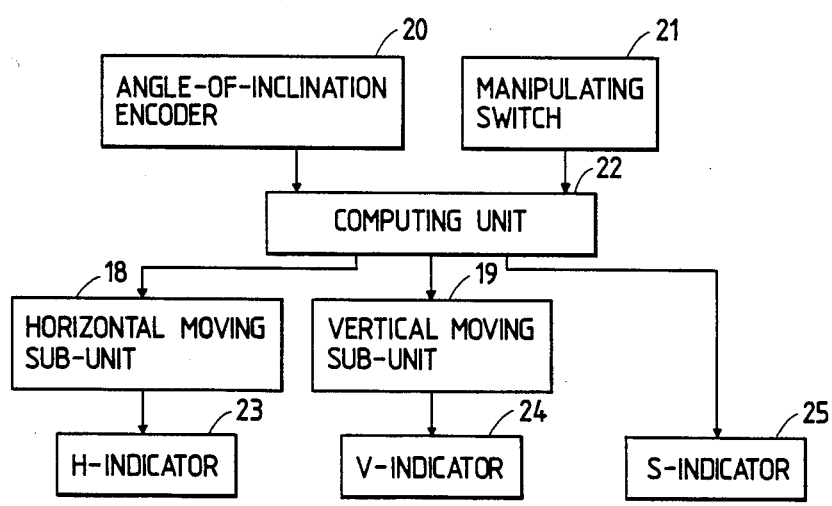
FIG. 2 is a block diagram of control circuitry in the apparatus shown in FIG. 1.

The CT apparatus shown in FIG. 1 has control circuitry which, as shown in FIG. 2, comprises an angle-of-inclination encoder 20 which detects the angle of inclination ($\alpha$) of the gantry 1 and which outputs the detected angle after it is converted to an electric signal, a computing unit 22 which computes the amount of movement on the basis of the output signal for angle of inclination and a movement command signal from a manipulating switch 21, the horizontal moving sub-unit 18, the vertical moving sub-unit 19, and units 23, 24 and 25 for indicating the amounts of movements in a horizontal direction (H), a vertical direction (V) and a composite or synthesized direction (S), respectively.

Examination of a subject with the apparatus shown above is conducted by the following procedure. First, the subject 2 is seated on the holder 3 which is a chair, with the angles of a back rest 26, a head rest 27 and other parts of the holder 3 being adjusted appropriately, and the subject is secured with belts or some other suitable device. The head of the subject is securely held against the head rest 27.

Figure 3:
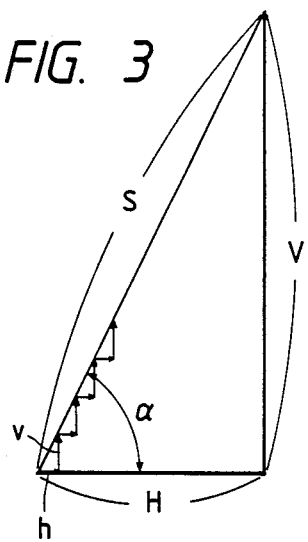
FIG. 3 is a diagram showing the directions in which a subject holder in the apparatus is to be moved.

The vertical position of the gantry 1 and the angle of its rotation are roughly set by means of the drive unit 12, and the holder 3 is moved by means of the moving unit 17 in such a way that the head of the subject 2 approaches the tunnel 10 in the gantry 1. Three projectors 31 are incorporated at the entrance of the gantry 1 so that they are arranged in the same plane perpendicular to the axis 28 of the tunnel 10 and that, when the head is located at the entrance portion, they are positioned above the head and at the both sides of the ears, respectively. Each projector 31 projects a cross pattern of light. One line of the cross pattern of light from each of the side projectors 31 is brought into alignment with the OM line (the line connecting the outer canthus and the earhole) of the head while the center of the cross pattern is brought into alignment with the earhole. At the same time, one line of the cross pattern of light from the top projector 31 is brought into alignment with the line connecting the eyes while the other line of the cross pattern with the median line of the face. By these adjustments, the axis of the subject 2 is made coincident with the axis 28 of the tunnel 10. When the manipulating switch 21 is depressed, a movement command signal is produced and sent to the computing unit 22 together with the signal for angle of inclination of the gantry 1 being supplied from the encoder 20. The computing unit 22 supplies the horizontal moving sub-unit 18 of the moving unit 17 with pulses for causing a movement for a preset time (see FIG. 3) and, as a result, the holder 3 is moved horizontally by a small distance (h). Subsequently, the computing unit 22 also supplies the vertical moving sub-unit 19 with pulses for causing a movement by a small distance (v) and this causes the holder 3 to move vertically by that small distance. In other words, the respective numbers of unit pulses which satisfy the relation $\tan \alpha = V/H = v/h$ are computed by the computing unit 22 on the basis of the data for angle of inclination ($\alpha$), and alternate movements in the horizontal and vertical directions will take place. As a result, the holder 3 moves in a direction perpendicular to the gantry 1 and causes the head of the subject to slide into the tunnel 10.

The indicators 23, 24 and 25 on a monitor display the amounts of movements in the horizontal, vertical and composite direction, respectively, of the holder 3 at each point of time, and the moving unit 17 is stopped when the holder reaches an optimum position.

Figure 4:
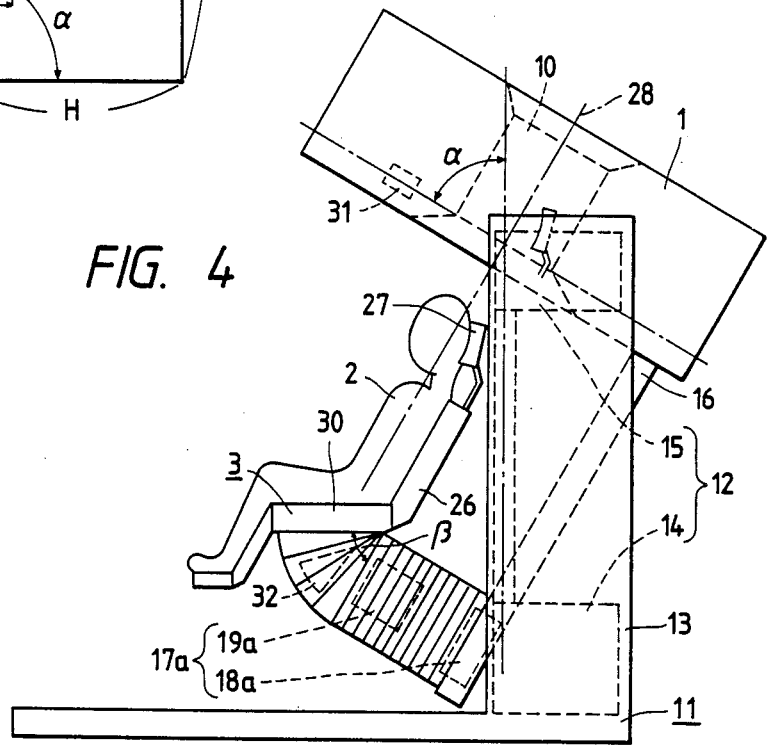
FIG. 4 is a front view of a CT apparatus according to a second embodiment of the present invention.
Figure 7:
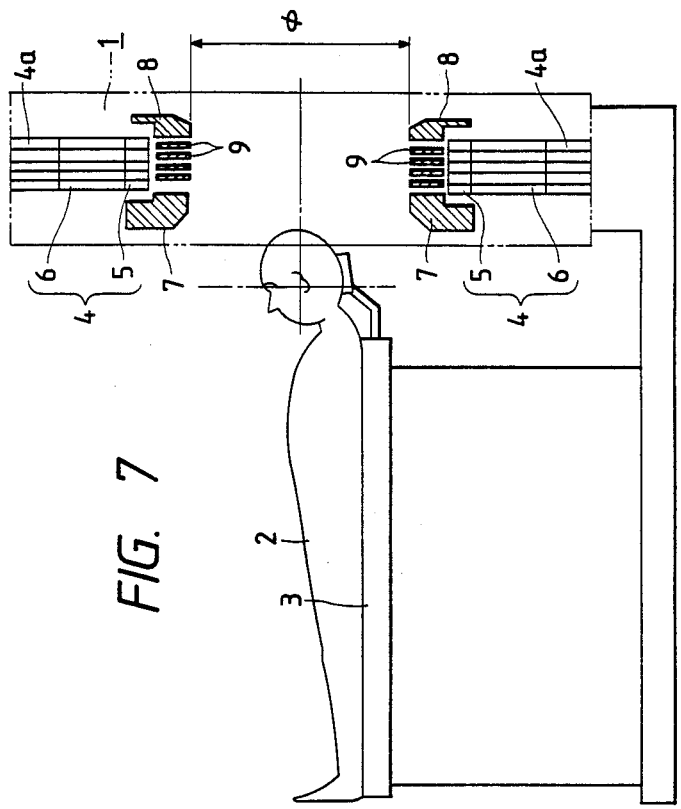
FIG. 7 is a front view of the CT apparatus of FIG. 6.

FIG. 4 shows another embodiment of the present invention, in which the gantry 1 is unitized with the rails 16 on which the holder 3 is provided. In this embodiment, the drive unit 12 consisting of the vertical drive sub-unit 14 and rotational drive sub-unit 15 drives the gantry 1 together with the holder 3. The holder 3 is also solely driven by a unit 17a which consists of sub-units 18a and 19a for linear movements perpendicular to each other and by a unit 32 for rotational movement.

Figure 5:
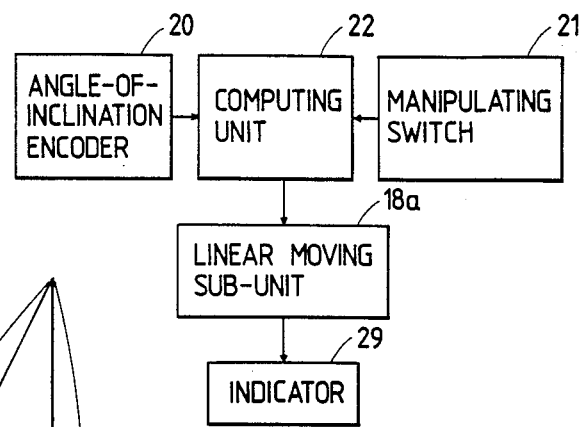
FIG. 5 is a block diagram of control circuitry in the apparatus shown in FIG. 4.

The control circuitry used in the second embodiment is shown in FIG. 5. As shown, it comprises an angle-of-inclination encoder 20, a computing unit 22, a manipulating switch 21, a sub-unit 18a for causing a linear movement in the direction of inclination, and an indicator 29.

In the second embodiment having the construction described above, adjustments are conducted using the three projectors 31 in the similar manner as the first embodiment so that the inclination direction of the gantry 1, i.e., the axis 28 of the tunnel becomes coincident with the axis 28 of the subject 2. In this embodiment, the angle of rotation of a seat 30, B, can be adjusted to become equal to the angle of rotation, $\alpha$, of the gantry 1 by operating the rotational drive sub-unit 15 in operative association with the unit 32 for rotational movement. After these adjustments, the sub-unit 18a for linear movement need only be operated to cause the head of the subject 2 to slide into the tunnel 10, with the distance of entry being displayed by the indicator 29.

According to the present invention, the site of a subject to be examined can be correctly positioned with respect to a measurement view range in the tunnel of a gantry without requiring much skill and yet in a safe and quick way. Further, the subject can be slid into the tunnel in alignment with its axis, so the diameter of the tunnel can be minimized to insure highly sensitive examination of the subject. The CT apparatus of the present invention has the additional advantage that it is capable of correct examination irrespective of whether the subject is in a supine or sitting position.

What is claimed is:

1. A computed tomography apparatus in which a gantry and a subject holder are supported on a main frame, said apparatus comprising:
   gantry drive means for moving said gantry to a position of examination, and driving said gantry until an inclination angle for examination is reached;
   computing means for performing mathematical operations based on data representing said inclination angle of said gantry set by said gantry drive means, and producing a control signal for controlling a holder moving direction which is determined in accordance with said inclination angle; and
   moving means for moving said holder in said holder moving direction in response to said control signal from said computing means.

2. A computed tomography apparatus according to claim 1, wherein said subject holder is a chair comprising a seat and a back rest which, when straightened out, will make up a bed.

3. A computed tomography apparatus according to claim 1, further comprising encoding means for detecting said inclination angle of said gantry, and producing an electric signal as said data.

4. A computed tomography apparatus according to claim 1, wherein said gantry is installed on support legs of said main frame in such a way that it is capable of both vertical and rotational movements, and said subject holder is installed on rails of said main frame in such a way that is capable of both horizontal and vertical movements.

5. A computed tomography apparatus according to claim 2, wherein said moving means moves said holder in said holder moving direction as a result of alternate small movements in a horizontal and vertical direction.

6. A computed tomography apparatus according to claim 1, wherein said gantry forms a unitary assembly with rails on which said subject holder is installed, and said gantry is installed on support legs of said main frame in such a way that it is capable of both vertical and rotational movements, with aid subject holder being installed on said rails in such a way that it is capable of a rotational movement, a first linear movement along said rails, and a second linear movement perpendicular to said first linear movement.

7. A computed tomography apparatus according to claim 3, wherein said moving means moves said holder in said holder moving direction by linearly moving said holder along said rails.

* * * * *

UNITED STATES PATENT AND TRADEMARK OFFICE
CERTIFICATE OF CORRECTION

PATENT NO. : 4,961,208
DATED : October 02, 1990
INVENTOR(S) : Hiroyuki Okada

It is certified that error appears in the above-identified patent and that said Letters Patent is hereby corrected as shown below:

Claim 6, Column 4, Line 68, "aid" should be --said--.

Signed and Sealed this

Fifth Day of January, 1993

Attest:

DOUGLAS B. COMER

Attesting Officer

Acting Commissioner of Patents and Trademarks